United States Patent

Yokoo et al.

[11] Patent Number: 5,567,231
[45] Date of Patent: Oct. 22, 1996

[54] DEODORANTS, DEODORANT SHEETS, FILTER SHEETS AND FUNCTIONAL PAPERS AS WELL AS FILTERING MEDIUMS FOR EXHAUST GAS

[75] Inventors: Akihiko Yokoo; Tetsuro Ogawa, both of Tokyo, Japan

[73] Assignee: Asahi Kogaku Kogyo Kabushiki Kaisha, Japan

[21] Appl. No.: 388,586

[22] Filed: Feb. 14, 1995

Related U.S. Application Data

[62] Division of Ser. No. 197,173, Feb. 16, 1994, which is a continuation of Ser. No. 840,586, Feb. 26, 1992, Pat. No. 5,310,548, which is a continuation of Ser. No. 512,323, Apr. 23, 1990, abandoned.

[30] Foreign Application Priority Data

| Apr. 21, 1989 | [JP] | Japan | 1-102355 |
| Apr. 28, 1989 | [JP] | Japan | 1-110993 |
| Nov. 2, 1989 | [JP] | Japan | 1-286120 |
| Jan. 10, 1990 | [JP] | Japan | 2-003198 |

[51] Int. Cl.$^6$ ............................. B01D 53/04
[52] U.S. Cl. .................. 96/153; 96/154; 55/524; 55/528; 55/DIG. 5; 55/DIG. 30
[58] Field of Search ............ 55/523, 524, 528, 55/DIG. 5, DIG. 10, DIG. 30; 96/135, 153, 154; 162/181.1, 181.2

[56] References Cited

U.S. PATENT DOCUMENTS

| 2,226,841 | 12/1940 | Barnhart | 162/181.2 X |
| 2,402,966 | 7/1946 | Linzell | 162/181.2 X |
| 3,342,669 | 9/1967 | Boggess | 162/181.2 |

(List continued on next page.)

FOREIGN PATENT DOCUMENTS

| 0274608 | 7/1988 | European Pat. Off. . |
| 3722102 | 1/1988 | Germany . |
| 55-124525 | 9/1980 | Japan .................... 96/154 |
| 57-12409 | 3/1982 | Japan . |

(List continued on next page.)

OTHER PUBLICATIONS

Derwent Abstract No. 87-318665: English language abstract of JP-A-62 227 932.
Derwent Abstract No. 88-094874: English language abstract of JP-A-63 044 997.
Derwent Abstract No. 85-084087: English language abstract of JP-A-60 035 016.
European Office Action and European Search Report.
English language abstract of Japanese Patent Publication No. 61-47401.
English language abstract of Japanese Patent Publication No. 59-95931.
English language translation of pertinent portions of Japanese Patent Publication No. 58-31200.
Decision of Refusal and an English Language Translation thereof.

*Primary Examiner*—Robert Spitzer
*Attorney, Agent, or Firm*—Greenblum & Bernstein P.L.C.

[57] ABSTRACT

Deodorant comprising 5 to 100% by weight of a calcium phosphate compound having a molar ratio of Ca/P of 0.8 to 2.0, a deodorant sheet and filter sheet containing such calcium phosphate compound, and a functional paper containing 10 to 80% by weight of a calcium phosphate compound. A filtering medium for an exhaust gas comprises a ceramic material containing 5 to 100% by weight of a calcium phosphate compound, as well as a filter cartridge and exhaust gas filter containing the filtering medium. Based on the excellent properties of the incorporated calcium phosphate compound, the agents and products according to the present invention exhibit a highly improved adsorptivity to oil-soluble substances, odor substances, animal or vegetable cells, viruses, biopolymeric substances or other substances, and therefore can be advantageously used in various fields of technology. For example, the functional paper can be used as a deodorant, filter medium and adsorbent as well as a flame-retardant paper. The filtering medium, filter cartridge and filter can be used in an exhaust system to purify an exhaust gas produced therein.

12 Claims, 4 Drawing Sheets

U.S. PATENT DOCUMENTS

| | | | |
|---|---|---|---|
| 4,126,473 | 11/1978 | Sobolev et al. | 162/181.2 X |
| 4,395,357 | 7/1983 | Kramer et al. | 252/428 |
| 4,568,538 | 2/1986 | Boden | 514/788 |
| 4,699,681 | 10/1987 | Kasmark, Jr. et al. | 96/154 X |
| 4,708,959 | 11/1987 | Shroot | 514/373 |
| 4,761,366 | 8/1988 | Nakajima | 435/2 |
| 4,948,787 | 8/1990 | Chen | 514/141 |
| 5,017,268 | 5/1991 | Clitherow et al. | 162/181.1 X |
| 5,113,666 | 5/1992 | Parrish et al. | 96/154 X |
| 5,288,298 | 2/1994 | Aston | 96/154 X |
| 5,289,695 | 3/1994 | Parrish et al. | 96/154 X |
| 5,328,758 | 7/1994 | Markell et al. | 96/154 X |
| 5,350,443 | 9/1994 | von Blücher et al. | 96/154 X |
| 5,379,681 | 1/1995 | Rollen | 96/135 X |

FOREIGN PATENT DOCUMENTS

| | | | |
|---|---|---|---|
| 58-31200 | 2/1983 | Japan . | |
| 58-91048 | 5/1983 | Japan . | |
| 59-95931 | 6/1984 | Japan . | |
| 59-142843 | 8/1984 | Japan . | |
| 60-35016 | 2/1985 | Japan . | |
| 60-100559 | 7/1985 | Japan . | |
| 61-47401 | 3/1986 | Japan . | |
| 62-227932 | 10/1987 | Japan . | |
| 63-44997 | 2/1988 | Japan . | |
| 63-267421 | 11/1988 | Japan . | |
| 5-154329 | 6/1993 | Japan | 96/154 |
| 68-5457 | 8/1968 | South Africa . | |
| 81-02891 | 10/1981 | WIPO . | |
| 90-03219 | 4/1990 | WIPO . | |
| WO94/08086 | 4/1994 | WIPO | 162/181.1 |

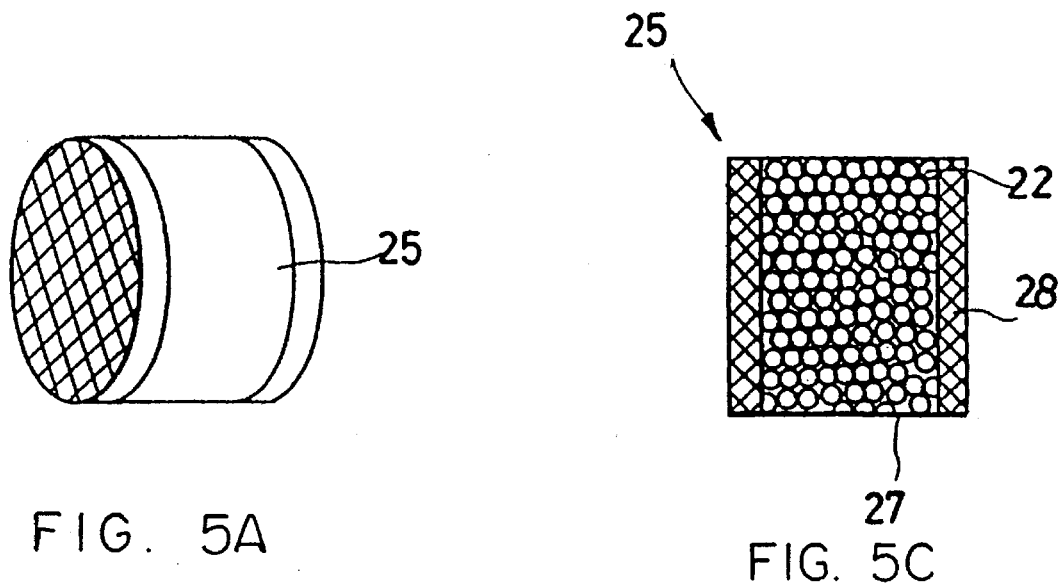
FIG. 5A
FIG. 5C
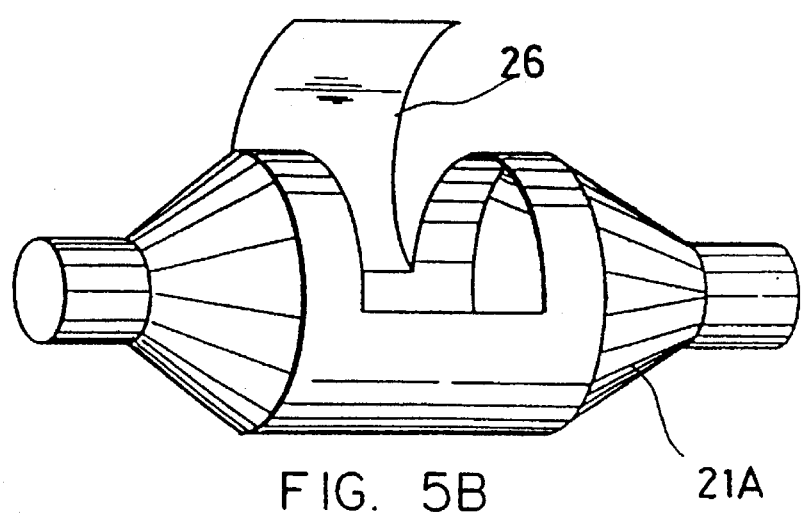
FIG. 5B

DEODORANTS, DEODORANT SHEETS, FILTER SHEETS AND FUNCTIONAL PAPERS AS WELL AS FILTERING MEDIUMS FOR EXHAUST GAS

This application is a division, of application Ser. No. 08/197,173, filed Feb. 16, 1994, pending, which is a continuation of Application Ser. No. 07/840,586, filed Feb. 26, 1992, which issued as U.S. Pat. No. 5,310,548 on May 10 1994, which is a continuation of 07/512,323, filed Apr. 23, 1990, now abandoned.

BACKGROUND OF THE INVENTION

1. Field of the Invention

The present invention relates to improved agents and products containing a calcium phosphate compound. More particularly, the present invention relates to a deodorant which can adsorb and remove different odor components. The present invention also relates to a functional sheet, especially a deodorant sheet containing the above deodorant, and a filter sheet which selectively traps a biological polymeric substance, bacterium, virus, animal or vegetable cell, toxic gas, odor component, dust or mist in a gas or liquid, but allows a permeation of other components. The present invention also relates to a functional paper used in different fields of technology, and is especially used as a deodorant, filtering medium and adsorbent. Also, the present invention relates to a filtering medium and filter cartridge for an exhaust gas as well as an exhaust gas filter. The filtering medium, filter cartridge and exhaust gas filter are disposed in an exhaust system to purify an exhaust gas. They can effectively trap soot or carbon dusts and also adsorb gaseous substances such as carbon monoxide or hydrocarbons, without causing a blocking of the pores of the filtering medium.

2. Description of Related Art

Hitherto, to remove any odor components or substances from the surrounding atmosphere or the like, many odor removing processes have been widely used, and typical examples of the well-known deodorizing processes include (1) the use of an aromatizing agent or fragrance to mask the odor, (2) the use of a catalyst to chemically decompose odor components to thereby make them odorless, and (3) the use of an adsorbent capable of adsorbing and removing any odor components. However, each of these three processes has problems to be solved.

For example, the aromatizing agent can sometimes emit an unpleasant smell to a person, because generally it must be an agent capable of emitting a strong fragrance in comparison with the odor components. The catalytic decomposition of the odor components is limited to only some of the odor components, because there is no known catalyst which is effective for all odor components. In addition, activated carbon, which is a typical example of well-known adsorbent-type deodorant, cannot effectively adsorb basic gases such as ammonia gas, although it can adsorb substantially all other odor components. Further, activated carbon must be used under conditions of low temperature, because it can be easily removed at an elevated temperature as a result of combustion. It is therefore desirable to provide an improved deodorant which is effective for all types of odor components and does not restrict the conditions of the usable working temperature.

In connection with the above-described adsorbents as a deodorant, it should be noted that hitherto, a fibrous substance such as filter paper or filter cloth, granular substance such as activated carbon, clay, gravel or diatomaceous earth, or porous substance such as porous pottery have been used as a filtering medium. Apparently, almost all of these filtering mediums are used to trap solid substances, and suitable filtering mediums are selected depending on the specific solid substances to be trapped or filtrated. However, the prior art filtering mediums suffer from some drawbacks.

Activated carbons has frequently been used as a filtering medium, because it exhibits an excellent adsorptivity. However, since it has no adsorption power for any oil-soluble substances or any malodorous components such as ammonia, activated carbon cannot be used to remove these substances and components from any gas liquid containing the same.

Recently, a membrane filtering system has been developed, but it suffers from a high production cost, because it is essential to use an ultrafiltration membrane or reverse osmosis membrane. On the other hand, a bacterial filter such as a suite filter has also been developed. However, the use of this filter is limited to the trapping of bacteria, and if used, the filtration must be carried out under conditions of reduce pressure or centrifugal force. As one will appreciate from the above the prior art filtering mediums can only be applied to a limited range of substances to be filtered off, or require expensive filtering equipment.

Turning the discussion of the prior art to functional paper, as is well-known in the art, in the production of conventional white-colored papers, a filler is used to improve the opacity, smoothness, ease of writing, ink-receptivity and other properties of the papers. Typical examples of such filler include clay, talc, titanium white, calcium carbonate and the like.

Further, it is also well-known to produce ceramic paper from a pulp, skeleton material and fixing material, in accordance with paper production technology. However, the prior art methods are nos suitable for the production of ceramic papers having a high flexibility equivalent to that of plain papers.

Furthermore, Japanese Unexamined Patent Publication (Kokai) 59-95931 teaches the production of papers having special functions in accordance with the specified method. The papers produced in accordance with this method contain finely divided particles of crystalline aluminum orthophorphate, and are characterized by their good capability of adsorbing odor components or substances. These functional papers can effectively adsorb odor substances such as ammonia, but cannot adsorb other odor substances.

Moreover, recently, developments and research for an exhaust gas filter, and a filtering medium and filter cartridge for the filter, have been extensively carried out to prevent air pollution.

Exhaust gases from an internal combustion engine or the like, for example, those from automobiles, contain nitrogen oxides $NO_x$, soot or carbon dusts, carbon monoxide CO, hydrocarbons, and other gaseous substances. Since these substances cause air pollution, the discharge of such exhaust gases into the atmosphere is now controlled by air pollution control regulations or similar acts. The current regulations are generally directed to control of the nitrogen oxides only. However, as a recent development, the regulations have been expanded to also cover the control of soot dusts, carbon oxide and hydrocarbons discharged from diesel engines.

Previously, to remove fine dusts such as soot dusts from the exhaust gas discharged from a diesel engine, it has been conventional to pass the exhaust gas through a porous filter, such as cordierite or a fibrous filter, such as quartz glass fibers or metallic fibers. The dusts are physically trapped by this porous or fibrous filter, and then heated to cause combustion thereof. However, the porous or fibrous filter has a drawback in that back pressure can increase due to the frequent blocking of the pores of the filter. It is also conventional to use a porous filter with a plurality of open pores in which each gas passage has a coating of an oxidation catalyst applied thereon. However, due to the complicated production process thereof, porous filters suffer from a high production cost and a low dust trapping efficiency.

SUMMARY OF THE INVENTION

One object of the present invention is to provide an improved deodorant which can adsorb and remove all types of malodorous components including ammonia, and can be used at both lower and higher temperatures. Another object of the present invention is to provide an improved filter sheet which can be produced at a low cost, has a simplified structure, can be easily handled, and can effectively trap any gaseous substances, bacteria, viruses, animal and vegetable cells and other substances, in addition to solid substances.

Another object of the present invention is to provide a functional paper which has a wide variety of adsorption functions and therefore can be used in the adsorption of ammonia and other odor substances, in addition to finding general use as a writing paper printing paper and wrapping paper.

It is also desirable to provide an improved functional paper which is useful multipurpose paper.

Still another object of the present invention is to provide an improved filter medium which does not result in blocking of the pores thereof, can be easily produced, has a high trapping efficiency of soot or carbon dusts and other dusts, and exhibits a high adsorption performance (action) with regard to gaseous substances such as carbon monoxide or hydrocarbons. Further, it is desirable to provide an improved filter cartridge and exhaust gas filter using the improved filter medium.

Furthermore, it is desirable to provide an improved exhaust gas filter which exhibits a remarkably increased adsorption efficiency, ensures a uniform diffusion of the exhaust gas throughout the filter, and prevents a partial blocking of the filter pores due to unevenness of the load of the exhaust gas to the catalyst.

The above-described objects of the present invention, and other objects which will be appreciated from the following description, can be accomplished by using a calcium phosphate compound having an excellent selective adsorptivity and other good properties in accordance with the present invention.

In one aspect of the present invention, there is provided a deodorant which comprises 5 to 100% by weight of a calcium phosphate compound having molar ratio of calcium to phosphorus (Ca/P) of 0.8 to 2.0.

In another aspect of the present invention, there is provided a deodorant sheet which comprises a sheet-like support carrying powders, granules or porous granules of a calcium phosphate compound having a molar ratio of Ca/P of 0.8 to 2.0.

In another aspect of the present invention, there is also provided a filter sheet which comprises a sheet-like matrix of organic polymeric material having dispersed therein granules of a calcium phosphate compound having a molar ratio of Ca/P of 0.8 to 2.0.

In still another aspect of the present invention, there is provided a functional paper which contains 10 to 80% by weight of a calcium phosphate compound as a paper making filler.

Further, in one aspect of the present invention, there is provided a filtering medium for an exhaust gas which comprises a ceramic material containing 5 to 100% by weight of a calcium phosphate compound.

In another aspect of the present invention, there is provided a filter cartridge for an exhaust gas which comprises a container, at least a part of the wall of which is made of a gas-permeable material through which the gas is introduced and discharged, and a filter medium charged in the container, the filtering medium comprising a ceramic material containing 5 to 100% by weight of a calcium phosphate compound.

In still another aspect of the present invention, there is provided an exhaust gas filter which comprises a rectangular and hollow body and two or more plates of a filtering medium disposed in a hollow portion of the body, the filtering medium comprising a ceramic material containing 5 to 100% by weight of a calcium phosphate compound, and in which each of the plate of the filtering medium have a length which is shorter than the height of the hollow portion and are alternately attached to an upper and lower wall of the body at a certain distance between the plates so that a curved and extended flow route of the exhaust gas is created in the hollow portion.

In still another aspect of the present invention, there is also provided an exhaust gas filter which comprises a body of wire mesh and a granular filtering medium filled in the wire mesh body, the filtering medium comprising a ceramic material containing 5 to 100% by weight of a calcium phosphate compound having a molar ratio of calcium to phosphorus of 0.8 to 2.0, and a granule of the ceramic material having a granule size of 200 μm to 10 mm and a porosity of 5 to 75%, and in which the granule size of the ceramic material is gradually reduced in the direction of from an inlet side of the exhaust gas to an outlet side of the same.

In still another aspect of the present invention, there is also provided an exhaust gas filter which comprises a body containing a monolithic filtering medium having a pore size of 100 μm to 5 mm and a porosity of 20 to 80%, the filtering medium comprising a ceramic material containing 5 to 100% by weight of a calcium phosphate compound having a molar ratio of calcium to phosphorus of 0.8 to 20, and in which the pore size of the filtering medium is gradually reduced in the direction of from an inlet side of the exhaust gas to an outlet side of the same.

In still another aspect of the present invention, there is also provided an exhaust gas filter which comprises a ceramic material containing 5 to 100% by weight of a calcium phosphate compound, and in which the ceramic material in an inlet side of the exhaust gas is that sintered at a higher temperature than the ceramic material in an outlet side of the exhaust gas.

According to the present invention, as described hereinafter in detail, many advantages which could not have been obtained in the prior art deodorants and other related agents and products can be obtained.

First, the deodorant according to the present invention exhibits its excellent deodorizing effects at a wide working temperature of from a lower temperature to a higher temperature and accordingly can be widely used in different fields. Note, the deodorant is effective for an adsorption and separation of specific gases such as carbon monoxide which could not be removed by the prior art deodorants. Further, since the calcium phosphate compound used as a principal component of the deodorant has a white color. it is aesthetically acceptable and therefore can be used in the production deodorant-incorporated papers such as white-colored papers or valuable papers, for example, colored papers and textured or pattern-printed papers.

Second, the filter sheet of the present invention is low-priced, has a simple structure, can be easily produced and handled, and can effectively trap any gaseous substances, viruses or bacteria, and animal or plant cells, in addition to filtering off of the solid substances. Further, since it has a sheet structure, the filter sheet can be easily inserted into and removed from filter equipment, and can be freely and easily replaced with a new filter sheet, when its adsorptivity has been reduced. Based on these advantages, the filter sheet can be applied to different filter and separation apparatus, for example, air cleaning equipment, water purifiers, deodorizing apparatuses, virus or bacteria filters, cell separators, serum filters and masks.

Third, the functional paper of the present invention is easy to handle, because it has a good flexibility like conventional papers. In addition to its use as a writing paper, printing paper and wrapping paper, the functional paper can be used to adsorb any oil-soluble substances which could not be adsorbed with a conventional activated carbon adsorbent, or any odor substances including ammonia, because it has a high adsorptivity due to specific properties of the calcium phosphate compound used as the filler. Further, since the calcium phosphate compound has a good biocompatibility, the functional paper can be used to adsorb any biological components such as animal or plant cells, virus, fractions of cell tissue, biopolymers and other components. Furthermore, with an increased amount of the calcium phosphate compound, the resulting functional paper can be used as a flame-retardant paper.

Fourth, since the filtering medium of the present invention contains a calcium phosphate compound having an excellent exhaust gas adsorption action, it can effectively adsorb gaseous substances such as carbon monoxide or hydrocarbons, in addition to dusts such as soot dusts, and therefore ensures a notably increased purification efficiency for the exhaust gas in contrast with the prior art filtering medium. Also, it can avoid the problem of the blocking of the pores thereof.

Further, since the filtering medium can be fabricated into a filter cartridge, the used filtering medium can be easily exchanged for a new one after a predetermined time of operation. Accordingly, it is always possible to conduct an effective purification of the exhaust gas, while the used filtering medium can be regenerated in a heat treatment or other regeneration treatment.

Furthermore, the exhaust gas filter of the present invention can provide a high purification efficiency due to the excellent characteristics of the filtering medium per se used therein, and also can significantly increase the purification efficiency of the exhaust gas due to the diffusion of the exhaust gas throughout the filtering medium thereof. In addition to these advantages, since a load is uniformly applied over the filtering medium of the filter, it becomes possible to avoid local blocking of the pores due to incorporation of soot and other dusts in the pores. Namely, it becomes possible to notably extend the useful life of the filtering medium, and accordingly to use the filter for an extended period of time. Moreover, in this connection, since deterioration of the filtering medium in the filter is caused at substantially the same degree and speed over a full cross section of the filter, it becomes possible to exchange all of the used filtering medium for a new one at once and then regenerate the same.

BRIEF DESCRIPTION OF THE DRAWINGS

FIG. 5A is a perspective view of the exhaust gas filter cartridge according to a preferred embodiment of the present invention;

FIG. 5B is a perspective view of the filter body in which the filter cartridge of FIG. 5A is contained;

FIG. 5C is a cross-sectional view of the filter cartridge of FIG. 5A;

DESCRIPTION OF THE PREFERRED EMBODIMENTS

Figure 1:
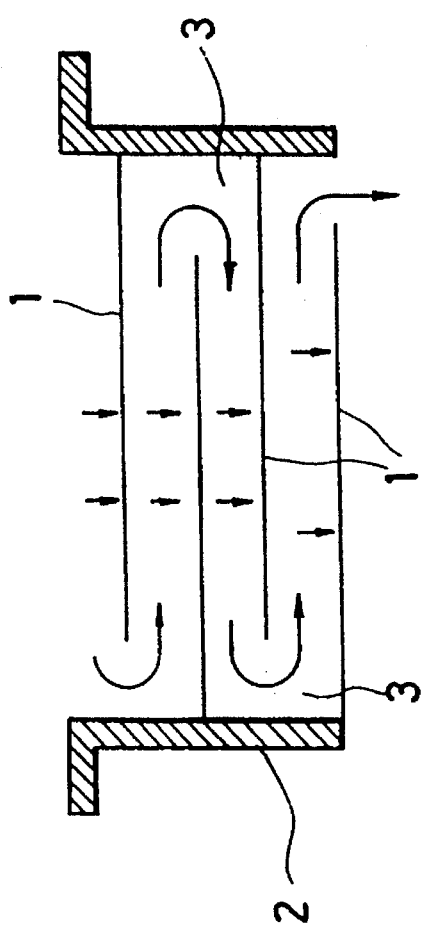
FIG. 1 is a cross-sectional view of the filter device containing a deodorant sheet according to the present invention.

The present invention will be further described with regard to preferred embodiments thereof.

The deodorant according to the present invention is characterized by comprising 5 to 100% by weight of a calcium phosphate compound having a molar ratio of calcium to phosphorus (Ca/P) of 0.8 to 2.0. Any calcium phosphate compounds having a Ca/P ratio of 1.0 to 2.0 can be preferably used in the practice of the present invention. However, in view of the characteristics of the calcium phosphate compounds and the strengths of the resulting granules, it is preferred that the calcium phosphate compounds exhibit a Ca/P ratio of 1.5 to 1.87. Typical examples of useful calcium phosphate compounds include apatites such as hydroxyapatite or fluoroapaptite, tricalcium phosphate, tetracalcium phosphate and other types of calcium phosphate compounds. These compounds may be used alone or in combination. Of course, these compounds can be produced in accordance with any conventional methods well-known in the field of ceramics production.

As described above, it is essential to the deodorant of the present invention that it contain at least 5% weight of the calcium compound. This is because no satisfactory deodorizing effect can be obtained if the calcium phosphate compound is used in an amount of less than 5% by weight.

Preferably, the calcium phosphate compounds are used in the form of powders, granules, porous granules or porous blocks, and are composed of a secondary particle produced from a primary particle having a particle size of 100 to 10,000Å through an aggregation or sintering thereof.

When the calcium phosphate compounds used are powders, granules or porous granules, it is preferred that they are carried on or in any sheet-like supports such as papers, nonwoven fabrics, mesh materials plastic foams. To produce a calcium phosphate compound-carrying support or deodorant sheet of the present invention, a variety of methods may be employed, for example, use of the calcium phosphate compound as a filler in the production of the papers or nonwoven fabrics or impregnation of the powders of the calcium phosphate compound from a slurry thereof into the support material.

For the production of papers containing the calcium phosphate compound powders as the filler, it is preferred that the powders as the filler are those comprising a secondary particle having a particle size of 0.1 to 30 μm. A particle size of less than 0.1 μm will cause a filteration of the particles together with water through the net structure of the paper production machine, while a particle size of more than 30 μm will cause an insufficient dispersion of the particles due to an excessively high weight thereof. The particle size of the powders or granules used herein can be suitably selected depending on various factors, such as specific properties of the gas-permeable materials or specific carrying manners.

For a deodorant sheet comprising a sheet-like support carrying the calcium phosphate compound granules, the granules generally have an average granule size of 0.1 to 200 μm, preferably 0.1 to 100 μm. If the granules have a size of less than 1 μm, they are hardly carried on the sheet-like supports. On the other hand, a granule size of more than 2000 μm means that the adsorbing effect is reduced as a result of the reduction of the contact area of the granules with air. Further, when the granules including porous granules are used in a container, it is preferred that the granules have a granule size of 200 μm to 10 mm. A granule size of less than 200 μm causes an increase in the resistance to air permeation, while a granule size of more than 10 mm causes a reduction in the adsorbing effect due to a reduced contact area between the granules and air.

The granular deodorant of the present invention may contain the calcium phosphate compound in at least a surface of the granules forming the deodorant. Therefore, the granular deodorant may have different types of configurations, for example:

(1) granules in which each granule entirely consists of one or more of the above-described calcium phosphate compounds;

(2) granules in which each granule consists of a core of a ceramic material other than the calcium phosphate compound, and a coating or shell of the calcium phosphate compound applied to a surface of the core, and;

(3) granules in which each granule consists of an inert carrier particle and a coating of the calcium phosphate compound applied to a surface of the carrier particle.

Further, when the calcium phosphate compound is used in the form of porous granules or porous blocks, it is preferred that they have a porosity of 5 to 75%. A porosity of less than 5% results in only insufficient deodorizing effect due to a low surface area of the granules or blocks, while a porosity of more than 75% causes a reduction of the strength of the granules or blocks.

Furthermore, the porous granules or blocks preferably have a specific surface area of 0.1 to 100 m²/g, more preferably 1 to 100m²/g. The specific surface area of less than 0.1 m²/g ensures only insufficient deodorizing effects, while the specific surface area of more than 100 m²/g causes a reduction of the strength of the granules or blocks, especially the blocks.

The porous granules and porous blocks of the calcium phosphate compound can be produced from a starting material, i.e., crystalline particles of the calcium phosphate compound prepared in accordance with the well-known wet process, according to any conventional manner. For example, a slurry of the suspended starting particles are spray-dried to directly make a secondary particle of the calcium phosphate compound. Or, after the slurry is mixed with any viscosity modifiers, organic compound particles capable of being burned off or sublimed upon heating and/or fibers, the mixture may be spray-dried to make a secondary particle of the calcium phosphate compound. The secondary particle is again slurried and then molded under wet process conditions, or molded under dry process conditions to make blocks of the calcium phosphate compound. In the production of the blocks, any organic compounds which are burned off or sublimed during the sintering process may be added to assist formation of pores in the blocks. Note, the absence of such organic compounds does not cause any inconvenience, because the size of the pores can be easily varied by changing other conditions or factors such as sintering temperature. The resulting block is sintered at a temperature of 500° to 1300° C. After sintering, the block is crushed and classified to obtain granules of the calcium phosphate compound having a desired granule size. Note, a sintering temperature of less than 500° C. should be avoided, because it causes an insufficient thermal vanishment of the organic compound or insufficient sintering of the block. On the other hand, any higher sintering temperature beyond 1300° C. causes an undesirable formation of the excessively dense sintered body or an undesirable decomposition of the calcium phosphate. The pore size of the granules can be modified by suitably controlling the size of the crystalline particles of the calcium phosphate compound for the production of the secondary particle, density of the slurry used and specific additive.

If desired, the deodorant of the present invention may contain any additives which are conventional in the production of deodorants, such as coloring agent or perfumes.

Since the deodorant of the present invention exhibits its good deodorizing effect at a wide range of temperatures from a lower temperature to a higher temperature, it can be effectively used in a plurality of products, or in different areas, for example, refrigerators, toilet rooms, containers for wet refuses, medical supplies such as diapers, sanitary napkins and bedsore pads, and innersoles. Further, since the deodorant absorbs harmful gases such as carbon monoxide or hydrocarbons, it can be disposed at an air blowing opening or air conditioners to remove bad smells the air-conditioned air during initial operation of the conditioner, or can be disposed at outlet of automobiles to remove an oily smell or bad smell of the gas from the exhaust gas. Furthermore, the deodorant can be disposed in odor-generating areas or exhaust vents in laboratories and factories, for example.

The filter sheet according to the present invention is characterized by comprising a sheet-like matrix of organic polymeric material and granules of s calcium phosphate compound having a Ca/P ratio of 0.8 to 2.0 dispersed in the matrix.

The organic polymeric matrix which can be used in the filter sheet of the present invention includes a wide variety of sheet-like materials, and typical examples of useful sheet-like materials are papers or cellulose materials, nonwoven fabrics and plastic foams such as urethane foams. The polymeric matrix used must contain sufficient air gaps to contain particles of the calcium phosphate compound therein, but for papers and nonwoven fabrics, gaps between the fibers are effective as such air gaps. Similarly, open cells of plastic foams are effective as such air gaps. The size of the gaps between the fibers and pore size of the open cells of the plastic foams are not limited in the practice of the present invention and therefore can be suitably selected depending on the specific size or amount of the granules to be dispersed in the matrix, but it is necessary that the gap size and pore size are sufficient to ensure permeation of the gas or liquid through the filter sheet, and contact of the gas or liquid with the granules of the calcium phosphate compound.

The thickness of the filter sheet of the present invention is not limited in the practice of the present invention and can be suitably selected depending on the specific use of the filter sheet. If desired, the filter sheets having a thickness of on the order of microns may be combined or superimposed to make a desired thickness.

For the filter sheet of the present invention, it is essential that the calcium phosphate compound used has a Ca/P ratio of 0.8 to 2.0, but any calcium phosphate compounds can be used in the practice of the present invention, insofar as they exhibit a Ca/P ratio of 0.8 to 2.0. Suitable calcium phosphate compounds are those previously described with regard to the deodorant of the present invention, i.e., apatite, tricalcium phosphate, tetracalcium phosphate or a mixtures thereof.

The calcium phosphate compound is used as granules, and preferably the granules of the calcium phosphate compound have a granule size of 0.1 to 100 µm. The granules, if they have a granule size of less than 0.1 µm, aggregate with each other to thereby prevent a dispersion of the granules in the polymeric matrix. On the other hand, for a granule size of more than 100 µm, the granules are hardly adhered to and carried by the polymeric matrix because of the excessively large size thereof. Moreover, the selection of the suitable granule size depends on the specific matrix used for example, if paper is used as the matrix, the granule size of the calcium phosphate compound used is preferably in the range of from 0.1 µm to 30 µm. A granule size of less than 0.1 µm will result in a discharge of the granules from a mesh of the paper making machine during the paper making process, while a granule size of more than 30 µm will result in nonuniform dispersion of the granules in the matrix because of the excessively high weight of the granules.

Preferably, the granules of the calcium phosphate compound have a porous structure. The porous granules of the calcium phosphate compound can be produced from a starting material, i.e., crystalline particles of the calcium phosphate compound, in accordance with the process which is similar to the process previously described with regard to the production of the porous granules and blocks for use in the production of the deodorant of the present invention. Note, the pore size of the porous granules varies depending on the specific substance to be trapped within the filter sheet. For example, if the specific substance is a virus or other organism, the porous granules should have a pore size of 0.01 µm or more.

Further, the porous granules of the calcium phosphate compound have a porosity of 10 to 75%. A porosity of less than 10% results in only insufficient surface area and water retention of the granules, while a porosity of more than 75% results in an unacceptably lowered strength of the porous granules. Preferably, the porous granules have a specific surface area of 1 to 150 m²/g.

Furthermore, the granules of the calcium phosphate compound may contain at least one additional active substance partially adsorbed on a surface thereof to modify physicochemical properties and immunological properties of the granule surface, and accordingly skillfully modify the adsorption activity of the granules. Suitable active substances include, for example, polysaccharides, such as living body-originated hyaluronic acid, chondroitin sulfate, chitin derivatives, fibronectin, osteonectin and the like, mucopolysaccharides and proteins, as well as derivatives thereof.

The filter sheet of the present invention can be advantageously produced in accordance with the following methods which however do not restrict the production of the filter sheet. For example, if paper or nonwoven fabric is used as the matrix, granules of the calcium phosphate compound can be added to the paper or fabric during their production. More particularly, when paper is used as the matrix, the granules of calcium phosphate are dispersed in a pulp slurry, and the mixture is processed to produce a desired filter sheet of the present invention. Similarly, when a nonwoven fabric is used as the matrix, the calcium phosphate compound is added to the starting material during the production of the fabric. When a plastic foam is used as the matrix, the plastic foam is immersed in a slurry of the calcium phosphate compound and then the impregnated plastic foam is dried to produce a desired filter sheet.

If desired, in the production of the filter sheet of the present invention, the filter sheet may be additionally perforated with a needle punch or other perforators to improve the permeability of the filter sheet to the gas or liquid to be filtered. The perforations in the matrix do not cause an undesirable permeation of the substances to be adsorbed by the calcium phosphate compound, because the calcium phosphate compound has a high adsorptivity and also is uniformly dispersed in the matrix, especially when the diameter of the perforations is not unduly increased.

Since the granular calcium phosphate compound dispersed in the matrix sheet has a good selective adsorptivity to biopolymeric substances, bacteria, viruses, animal and plant cells, toxic gases, malodorous components. dusts, mists and other noxious substances, the filter sheet of the present invention can be used as a filter in a wide variety of products which include, for example, air cleaning equipment, water purifiers, deodorizing apparatus, bacterium or virus filters, cell separators, serum filters and masks In addition to these wide uses, the used filter sheet having a reduced adsorptivity can be easily replaced with a new filter sheet, since its sheet structure makes the handling easy.

Moreover, if desired, the filter sheet of the present invention may be inserted between two gauze layers of a commercially available gauze mask or may be contained in a pocket of the gauze mask to improve the gauze mask. More particularly, the gauze mask with the filter sheet of the present invention can prevent an invasion of viruses, bacteria and the like into a human body, because the viruses and the like are adsorbed by the filter sheet. Remarkable effects are expected when such gauze mask is used during the prevalence period of influenza. Of course, the filter sheet can be easily inserted into and removed from the gauze mask.

The functional paper of the present invention is characterized by containing 10 to 80% by weight of a calcium phosphate compound as a filler.

In the practice of the present invention, a wide variety of calcium phosphate compounds maybe used as the filler. Typical examples of useful calcium phosphate compounds include apatites such as hydroxyapatite or fluoroapatite, tricalcium phosphate, tetracalcium phosphate and other types of calcium phosphate compounds. These compounds may be used alone or in combination.

The calcium phosphate compound is generally used as a powder and the power preferably comprises a secondary particle having a particle size of 0.1 to 30 µm. A particle size of less than 0.1 µm should be avoided, because it causes a passage of the powders together with water of the slurry through a net of the paper machine. On the other hand, a particle size of more than 30 μm will prevent uniform dispersion of the filler powders in the resulting paper due to the excessively high weights thereof. Preferably, the secondary particle is produced from the corresponding primary particle having a particle size of 100 to 10,000Å through an aggregation or sintering thereof.

In the functional paper of the present invention, it is essential that the above-described calcium phosphate compound filler is used in an amount of 10 to 80% by weight with regard to a total amount of the paper. An amount of filler of less than 10% by weight is not enough to fully obtain the expected functions of the functional paper, while an amount of more than 80% by weight causes a difficulty in obtaining paper-like products.

To obtain the best results, the amount of calcium phosphate compound used may be widely varied within the above-described range of 10 to 80% by weight depending upon the specific use of the functional paper. This is because the adsorption property of the functional paper relies upon the calcium phosphate compound and also can vary depending on the amount thereof. while the calcium phosphate compound has high, but different levels of adsorptivity for a plurality of substances including animal or plant cells. viruses, bacteria, biopolymeric materials, odor substances, tobacco tar and he like.

Generally, the calcium phosphate compound is used as the sole in the production of the functional paper. However, if desired, it may be used together with the conventional fillers such as clay, talc, titanium white or calcium carbonate.

The addition of the calcium phosphate compound as a filler in the paper can be preferably carried out in accordance with a filler-in-paper method in which the calcium phosphate compound is incorporated into the paper from a slurry of pulp in water, or a filler-on-paper method in which the calcium phosphate compound is applied to the paper from a coating solution containing the same. For the filler-on-paper method, it is contemplated to coat a combination of the filler and an adhesive capable of forming a three-dimensional network structure, as a coating solution, onto abase paper.

In any case, to attain the full benefit of the adsorption action of the calcium phosphate compound, it is preferred that the calcium phosphate compound have no coating applied onto a surface thereof. Also, it is preferred that the particles of the calcium phosphate compound used as a filler have a larger surface area. Such a larger surface area of the filler particles can be obtained, if the particles are aggregated or sintered to make finely divided porous particles having a particle size of 1 μm or less and containing a plurality of fine pores. Preferably, the filler particles have a specific surface area of 1 to 150 $m^2/g$ and the best specific surface area can be suitably selected with control of the pore size of the fine pores in the particles.

As previously described, the filler-in-paper method can be carried out by adding a selected amount of the filler to a slurry of pulp dispersed in an amount of water. If desired, a fixing agent may be added to the pulp slurry to inhibit flowing out of the filler from the paper machine. Suitable fixing agents include, for example, a modified polyethyleneimine, modified polyacrylamide, sodium alginate, gum arabic, soluble starch, aluminium sulfate or potassium alum. The amount of these fixing agents used can be suitably selected depending upon factors such as the type of fixing agent or the amount of calcium phosphate compound used.

The functional paper according to the present invention can be produced by adding powders of the calcium phosphate compound as a filler and other additives to a slurry of pulp. The pulp used herein has preferably a Canadian Standard freeness of 200 to 700cc. The additives used herein are those which are conventional in paper making, and include, for example, a sizing agent, dye and toughening agent. After intimate mixing, the mixture is fed into a conventional paper machine. Before the mixing of the filler with the pulp slurry, a surface active agent may be added to the slurry so that the filler can be effectively dispersed in the water of the slurry. The surface active agent used herein can be suitably selected from well-known anionic, cationic and nonionic surface active agents, taking the types of other additives and other factors into consideration.

The functional paper preferably shows a basis weight of 20 $g/m^2$ or more.

Since the functional papers of the present invention exhibit a high adsorptivity due to the presence of the calcium phosphate compound as a filler, they can be principally utilized in the following fields of application:

(a) deodorants

Since the functional paper can adsorb any odor substances, it can be used as a deodorant or deodorizer or a deodorant sheet with or without release of a perfume in, for example, medical supplies such as diapers, sanitary napkins and pads for bedsores, and innersoles.

(b) filter mediums

Utilizing a virus adsorptivity thereof, the functional paper can be used as a mask. Further, utilizing its capability of adsorbing and separating cells, the functional paper can be used as a filter for serum or blood. In addition, the functional paper can be used as a filter for removing proteins, filter medium for cigarettes or filter medium for air cleaners or water purifiers.

(c) adsorbents

Since the functional paper has a good biocompatibility and can adsorb any biopolymeric substance, it can be used as a filter paper for electrophoresis, filter paper for protein concentration, or substrate for chromatography, such as a filter paper for paper chromatography.

(d) substitute materials for biomaterials

The functional paper can be used as a tape for diaplasis, artificial skin, artificial blood vessel, artificial windpipe or drug-releasing system, for example.

(e) food wrapping papers (f) articles in the bioindustry

The functional paper can be used as a culture medium for cells, immobilizing carrier for enzymes or microorganisms, substrate for hydroponics or bioreactor, for example.

(g) articles in a medical treatment

The functional paper can be used as a clinical test paper, adhesive tape or endemic preparation, for example.

As previously described, the exhaust gas filtering medium of the present invention is characterized by comprising a ceramic material containing 5 to 100% by weight of a calcium phosphate compound. When the calcium phosphate compound is used in an amount of less than 5% by weight, only insufficient adsorption effects can be obtained. For the filtering medium of the present invention, it is enough to obtain satisfactory adsorption effects, if the calcium phosphate compound occurs in at least contact areas of the filtering medium with the exhaust gas. However, generally, it is preferred that the calcium phosphate compound is used in an amount of 50% by weight or more.

Preferably, the calcium phosphate compounds used in the present invention have a molar ratio of calcium to phosphorus (Ca/P) of 0.8 to 2.0. Typical examples of useful calcium phosphate compounds satisfying this requirement include apatites such as hydroxyapatite or fluoroapatite, tricalcium phosphate, tetracalcium phosphate and similar calcium phosphate compounds. These compounds may be used alone or as a mixture of two or more compounds.

The ceramic material of the filtering medium may comprise only the above-described calcium phosphate compound, or may comprise 5% by weight or more of the above-described calcium phosphate compound and a remainder of other types of ceramic materials. Typical examples of ceramic materials used in combination with the above-described calcium phosphate compound include silica, alumina, titania, zirconia, cordierite, zeolite and similar ceramic materials.

The filtering medium for the exhaust gas according to the present invention may have any desired structure. Preferably, the filtering medium has a granular structure, monolithic porous structure or honeycomb structure. The honeycomb structure can be obtained by molding the ceramic material in a suitable mold.

When the ceramic material as the filtering medium is a granular structure, it is preferred that each granule have a granule size of 200 μm to 10 mm and a porosity of 5 to 75%. A granule size beyond 10 mm will reduce purification efficiency of the exhaust gas as a result of the reduction of the contact area between the filtering medium and the exhaust gas. On the other hand, an excessively reduced granule size is inconvenient, because it causes an increased resistance to the passage of the exhaust gas. In summary, it is contemplated to totally consider the granule size and porosity of the granules before the selection thereof. Note, a relatively low porosity may be used, if the granule size is low, and the mechanical strength of the resulting filtering medium is lowered, if the porosity exceeds 75%.

The granular filtering medium of the present invention, as already described in the previous paragraph, may contain the calcium phosphate compound in at least a surface of the granules forming the filtering medium. Therefore, the granular filtering medium may have different types of configurations, for example:

(1) granules in which each granule entirely consists of one or more of the above-described calcium phosphate compounds;

(2) granules in which each granule consists of a core of a ceramic material other than the calcium phosphate compound, and a coating or shell of the calcium phosphate compound applied to a surface of the core, and;

(3) granules in which each granule consists of an inert carrier particle and a coating of the calcium phosphate compound applied to a surface of the carrier particle.

The above-described granules as a filtering medium of the present invention can be produced in accordance with any conventional methods which are well-known in the art. For example, the above-described granules (1) entirely consisting of the calcium phosphate compound can be produced in the same manner as described with regard to the granular deodorant.

When the ceramic material as the filtering medium has a monolithic porous structure, it is preferred that the porous structure have a pore size of 100 μm to 5 mm and a porosity of 20 to 80%. As in the above-described granular ceramic material, it is contemplated to totally consider the pore size and porosity of the porous structure before the selection thereof. Note, a pore size of less than 100 μm tends to cause blocking of the pores as a result of trapping of the dusts in the pores, while a pore size of more than 5 mm causes a reduction of the contact area of the filtering medium with the exhaust gas, thereby inducing a lowered purification efficiency of the gas. In addition, a porosity of less then 20% causes an increase in the back pressure and at the same time a reduction of the contact areas of the filtering medium with the exhaust gas, thereby inducing a lowered gas purification efficiency.

The filtering medium as a monolithic porous structure can be produced in accordance with the methods which are similar to that described above with regard to the production of the granular filtering medium. For example, the monolithic filtering medium can be produced by pulverizing a slurry of the starting calcium phosphate compound, which may be previously mixed with any particles of thermally decomposable organic compound or fibers, if necessary, with spray drying or other treatments to make a secondary particle of the calcium phosphate compound. The thus obtained secondary particle is molded into a molded product having the desired configuration, and the molded product is then defatted and sintered at a temperature of 500° to 1300° C. The monolithic filtering medium is thus obtained.

The filtering medium for the exhaust gas according to the present invention has a good adsorptivity because of the incorporated calcium phosphate compound, and therefore can effectively adsorb not only soot dusts and other dusts but also gaseous substances such as carbon monoxide or hydrocarbons including aliphatic and aromatic hydrocarbons. Further, since the calcium phosphate compound also has a good water absorption property, the filtering medium can additionally adsorb a water vapor in the exhaust gas, thereby further improving the gas adsorption efficiency of the filtering medium.

Furthermore, the filtering medium of the present invention can be easily regenerated by heating and firing the used filtering medium, although the adsorption efficiency of the filtering medium is reduced with time during the purification process of the exhaust gas. To accelerate this firing of the used filtering medium, it is preferred that at least a part of the surface of the filtering medium is coated with any suitable oxidation catalyst. Suitable oxidation catalysts include, for example, platinum catalyst or platinum-rhodium catalyst. The formation of the catalyst coating can be carried out in accordance with any conventional coating methods.

The filtering medium according to the present invention can be used to produce a filter cartridge for an exhaust gas. The filtering medium, for example, granular, monolithic or honeycomb ceramic material is charged in a, at least a part of the wall of which container is made from a gas-permeable material, preferably a wire mesh container. The configuration of the container is widely varied depending upon the specific use of the filter cartridge. Also, when the filtering medium has a monolithic or honeycomb structure, two or more parts of such filtering medium maybe combined to make an integral structure which is received in the container of the cartridge. Since the filter cartridge of the present invention is designed to be periodically exchanged with a new one and is easy to handle, the used filtering medium can be easily regenerated, and also the purification process of the exhaust gas can be carried out with a new filter cartridge, without interruption thereof, during regeneration of the used filtering medium.

As described in the above paragraphs, the filtering medium of the present invention can exhibit excellent performance and therefore can be widely used in different types of filter bodies to make an exhaust gas filter. The inventors found that if the filtering medium is effectively disposed in the filter body, the adsorption efficiency of the resulting filter can be further increased, the exhaust gas can be diffused throughout the filter, and a load of the gas can be uniformly applied to the filter, thereby providing an improved exhaust gas filter which does not cause a localized blocking of the filter pores.

In one embodiment of the present invention, the exhaust gas filter is characterized by comprising a rectangular and hollow filter body. Two or more plates of the filtering medium of the present invention are disposed at a predetermined interval in a rectangular hollow portion of the filter body to form a passage for the exhaust gas. Preferably, each plate of the filtering medium has a shorter length than the height of the hollow portion and is alternately attached or fixed to upper and lower walls of the filter body at a certain distance between the plates so that a curved and extended flow route of the exhaust gas is created in the hollow portion. More preferably, the plates of the filtering medium are disposed in parallel with each other and are perpendicular to a main flow direction of the exhaust gas.

In this exhaust gas filter, because of the presence of small gaps between the two adjacent plates of the filtering medium and between the wall of the filter body and the non-supported end of the filtering medium plate, a major amount of the exhaust gas introduced into the filter is permeated through a first plate of the filtering medium at an inlet side of the exhaust gas, while a minor amount of the introduced exhaust gas is guided through a gap between the first plate and the filter wall to the gap between the first and second plates, and a major amount of this gas is permeated through the second plate of the filtering medium. A remainder of the gas which could not be permeated through the second plate is combined with the gas permeated through the first plate, and then the combined gas is guided toward a third plate of the filtering medium. Apparently, the exhaust gas filter according to the described embodiment of the present invention is constituted such that the exhaust gas can be permeated, in sequence, through a series of filtering medium plates and therefore the gas can uniformly diffuse throughout the filter, with an uniform load.

To ensure uniformity of the load throughout the filter, it is preferred that the distance between the plates of the filtering medium is gradually reduced in the direction from an inlet side of the exhaust gas to an outlet side of the same. In the inlet side of the exhaust gas, a relatively large distance is applied between the filtering plates to increase the flow rate of the exhaust gas which is not permeated through the filtering plates, because an exhaust gas containing a higher concentration of pollution substances such as nitrogen oxides flows in such area. However, in an area near the outlet of the exhaust gas, a relatively small distance is applied between the filtering plates to thereby increase a flow rate of the exhaust gas permeated through the filtering plates. In this area, a lower concentration of pollution substances is contained in the flowing exhaust gas, in contrast to the area near the inlet of the exhaust gas.

In another embodiment of the present invention, the exhaust gas filter is characterized by comprising a filter body of wire mesh and a granular filtering medium of the present invention filled in the filter body. In this exhaust gas filter, the granule size of the ceramic material as the filtering medium is gradually reduced in the direction from an inlet side of the exhaust gas to an outlet side of the same. This distribution of granule sizes is effective for obtaining uniformity of the load onto the filtering medium.

In still another embodiment of the present invention, the exhaust gas filter is characterized by comprising a filter body having contained therein a monolithic filtering medium of the present invention. In this exhaust gas filter, the pore size of the filtering medium is gradually reduced in the direction from an inlet side of the exhaust gas to an outlet side of the same. This distribution of pore sizes is effective to attain uniformity of the load onto the filtering medium. Note, if desired, this embodiment and the two above-described embodiments may be freely combined to further improve excellent performance of the exhaust gas filter.

In each of the above-described embodiments, it is preferred that the ceramic material in an inlet side of the exhaust gas filter is that sintered at a higher temperature than the ceramic material in an outlet side of the exhaust gas filter. This distribution of sintering temperatures in the ceramic material as the filtering medium in the exhaust gas filter is effective for avoiding adverse influences due to introduction of the heated exhaust gas in the filter.

The present invention will be further described with reference to the accompanying drawings illustrating some preferred embodiments of the present invention.

FIG. 1 is a cross-sectional view of the filter device containing a deodorant sheet according to the present invention. The filter device comprises a rectangular box 2 with opened upper and lower walls. These two openings are used to introduce an ill-odored air into the filter device, and discharge the deodorized air therefrom, respectively. As illustrated, there are four deodorant sheets 1 of the present invention, and one end of each deodorant sheet 1 is alternately fixed to an opposed side wall of the box 2. This alternate arrangement of the deodorant sheets 1 is intended to form a zig zag flow path 3 of the air. The filter device is used in, for example, an air conditioner to remove bad odors from an air-conditioned air.

Figure 2:
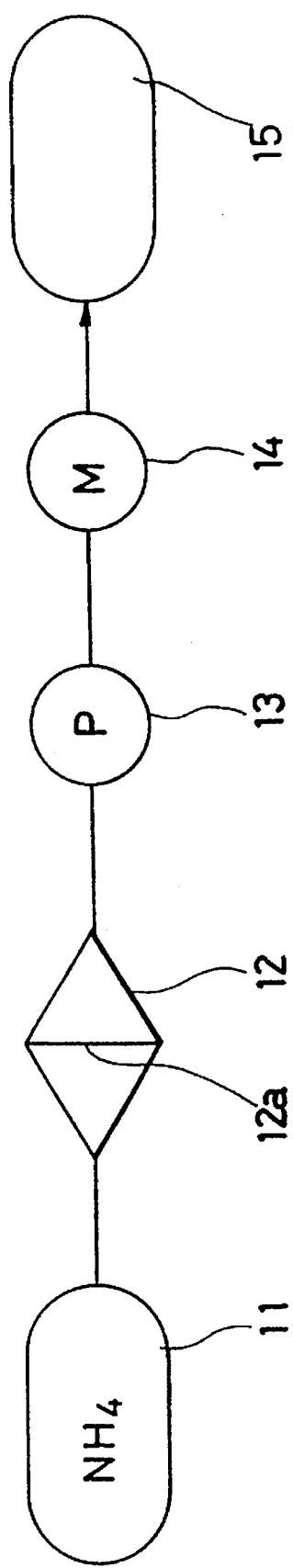
FIG. 2 is a flow diagram of the deodorizing apparatus in which the filter sheet of the present invention is used as a deodorant sheet.

FIG. 2 is a flow diagram of the deodorizing apparatus in which the filter sheet of the present invention is used as a deodorant sheet. The illustrated deodorizing apparatus comprises a teddler bag 11, a filter holder 12 with the filter sheet 12a, a pump 13, a flowmeter 14 and a teddler bag 15, which are connected through a tube in the recited order. The deodorizing apparatus of FIG. 2 is especially used to evaluate a deodorizing effect of the filter sheet.

Figure 3:
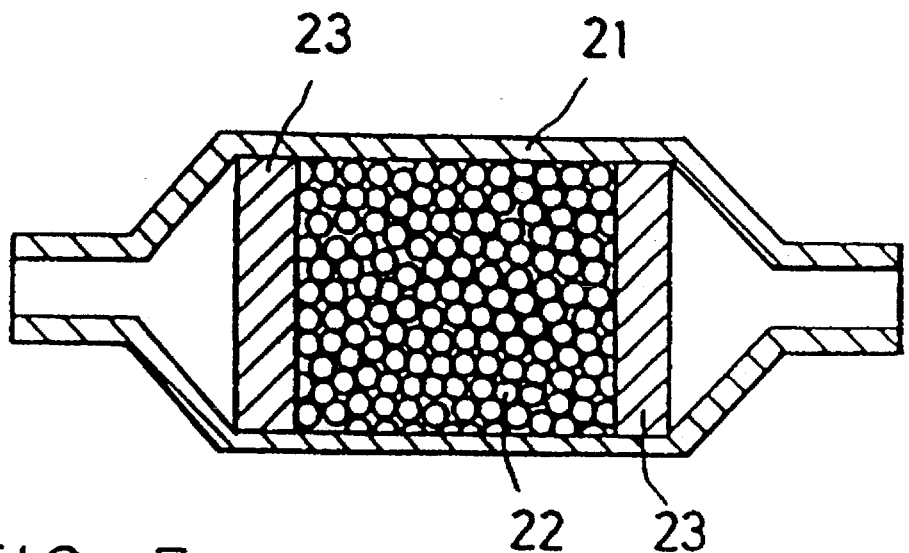
FIG. 3 is a cross-sectional view of the exhaust gas filter according to a preferred embodiment of the present invention.

FIG. 3 is a cross-sectional view of the exhaust gas filter of the present invention. The illustrated filter comprises a cylindrical filter body 21 and a granular filtering medium 22 contained in the filter body 21. The granular filtering medium 22 is fixedly retained with a pair of disc-shaped filtering mediums 23. The granular filtering medium 22 is one according to the present invention, but the disc-shaped filtering mediums 23 may be any conventional one. Practically, the disc-shaped filtering mediums are not restricted, insofar as they have a high heat resistance and can prevent a removal of the granular filtering medium from the filter body. Suitable disc-shaped filtering mediums include, for example, conventional ceramic filters and wire meshes.

In the exhaust gas filter shown in FIG. 3, soots and other dusts in the exhaust gas are principally trapped with the granular filtering medium 22, although some of them are trapped with the disc-shaped filtering medium 23. Further, since the filtering medium 22 has a good adsorptivity, it can absorb harmful gases such as carbon monoxide and hydrocarbon gases, in addition to the dusts. Accordingly, the gas discharged from the filter is a highly purified one and therefore exhibits a notably reduced concentration of substances which cause air pollution.

Figure 4:
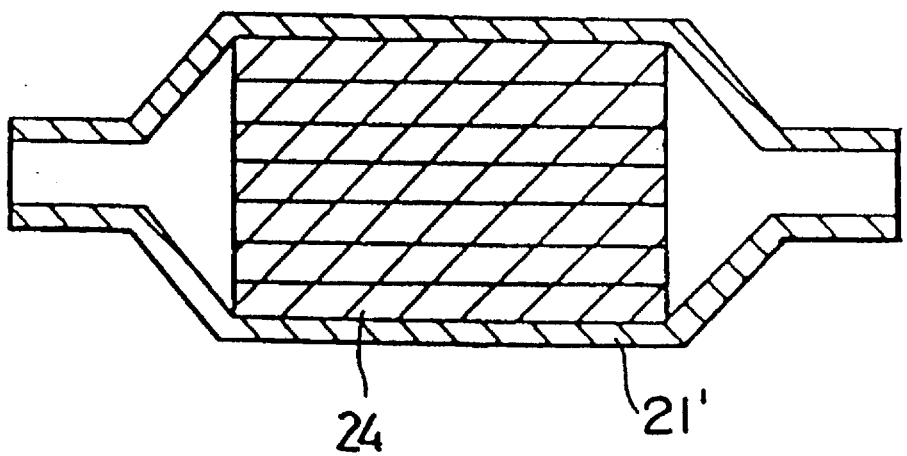
FIG. 4 is a cross-sectional view of the exhaust gas filter according to another preferred embodiment of the present invention.

FIG. 4 is a modification of the exhaust gas filter of FIG. 3 in which the granular filtering medium was replaced with a monolithic filtering medium of the present invention. As is illustrated in FIG. 4, porous parts 24 of the monolithic filtering medium are fixedly retained in a cylindrical filter body 21, but no disc-shaped filtering medium is contained therein. The porous parts 24 can selectively adsorb soot dusts and harmful gases such as carbon monoxide and hydrocarbon gases from the exhaust gas, while the gas is permeated through the parts. Accordingly, a clean air is discharged from the filter.

Although not illustrated, the exhaust gas filters of FIGS. 3 and 4 maybe provided with a heater means to burn and remove any substances adsorbed onto the filtering medium. It is contemplated to dispose the heater means around the cylindrical filter bodies 21 and 21'.

FIG. 5A is a perspective view of the filter cartridge for an exhaust gas filter according to the present invention. The illustrated filter cartridge 25 can be contained in, for example, a cylindrical filter body 21A of FIG. 5B. To ease an insertion and removal of the filter cartridge 25, the cylindrical filter body 21A has a movable covering 26. The covering 26 is designed to be easily opened or closed. FIG. 5C is a cross-sectional view of the filter cartridge of FIG. 5A. As shown in FIG. 5C, the filter cartridge 25 for the exhaust gas comprises a granular filtering medium 22 filled in a cylindrical casing 27. Both open ends of the casing 27 are closed with a cover 28 of wire mesh. The wire mesh cover 28 is effective to prevent removal of the filtering medium 22 from the cartridge 25, and also the filter cartridge 25 with the wire mesh covers 28 is easy to handle.

Figure 6:
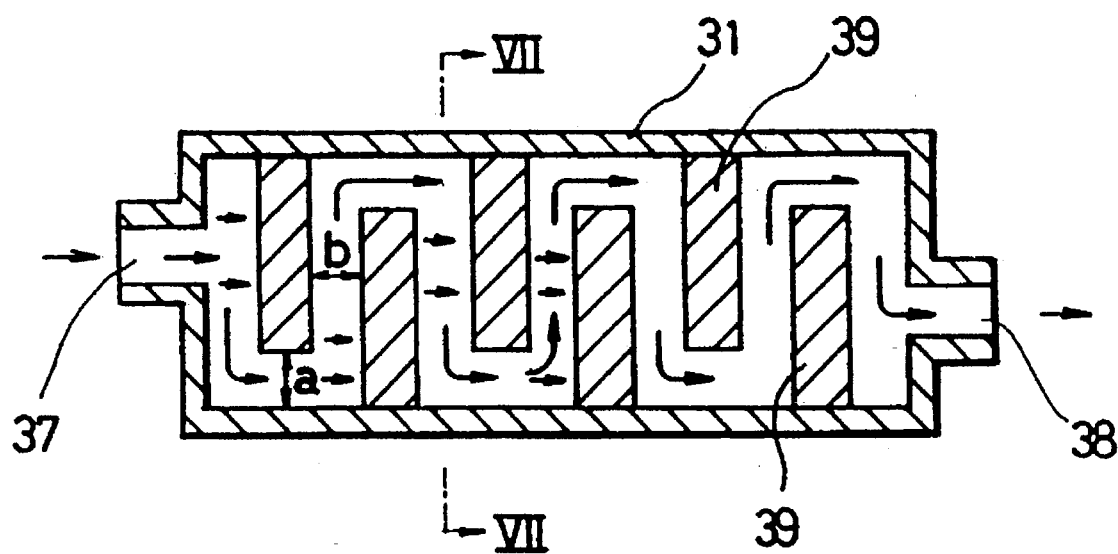
FIG. 6 is a cross-sectional view of the exhaust gas filter according to another preferred embodiment of the present invention.
Figure 7:
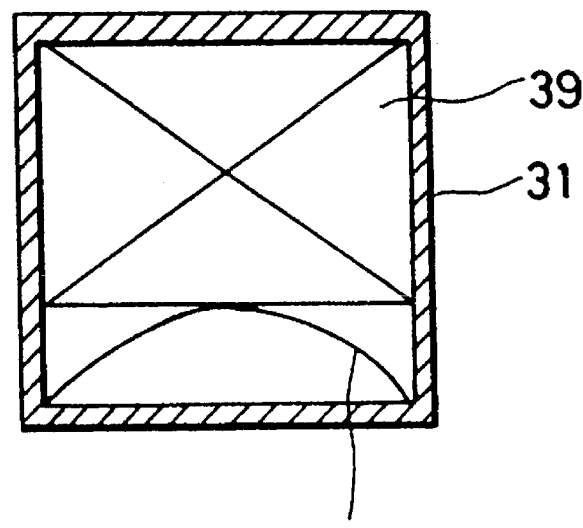
FIG. 7 is a cross-sectional view of the filter of FIG. 6 takes along line VII—VII.

FIG. 6 is a cross-sectional view of the exhaust gas filter according to another preferred embodiment of the present invention, and FIG. 7 is a cross-sectional view of the exhaust gas filter taken along line VII—VII of FIG. 6. The illustrated exhaust gas filter comprises a rectangular and hollow filter body 31, and the exhaust gas to be purified is guided in the hollow portion of the filter body 31 as shown with arrows in FIG. 6. The exhaust gas is introduced from an inlet 37 of the filter body 31 and the purified exhaust gas is discharged from an outlet 38 thereof. As is illustrated in FIG. 6, a plurality of plate-shaped filtering mediums 39 are alternately disposed at a predetermined distance in the hollow portion of the filter body 31. The means fixing filtering mediums 39 to an upper or lower wall of the filter body 31 is not restricted, but preferably, as shown in FIG. 7, the filtering mediums 39 may be removably attached through a leaf spring 40 or other spring means to the wall of the filter body 31.

In the exhaust gas filter of FIG. 6, a distance "a" between an end of the filtering medium 39 and an upper or lower surface of the wall of the filter body 31 and a distance "b" between the two adjacent filtering mediums 39 may be the same from the inlet 37 to the outlet 38 of the filter body 31. However, it is preferred that the distances "a" and "b" are gradually reduced in the direction from the inlet 37 to the outlet 38 to thereby ensure uniform load of the exhaust gas throughout the filter. Namely, this uniformity of load is ensured, because the exhaust gas containing an increased concentration of the toxic substances flows at a higher flow rate in the inlet area of the filter, but its flow rate is gradually reduced with reduction of the concentration of the toxic substances in the gas.

In the exhaust gas filter shown in FIG. 6, each filtering medium 39 can be easily introduced into and removed from the filter body 31, if one side wall of the filter body 31 is designed to be removable. Practically, the filtering mediums can be more easily handled through a smaller side opening of the filter body, in comparison with the above-described cylindrical filter.

The present invention will be further described with reference to some working examples which do not restrict the scope of the present invention.

EXAMPLE 1

A hydroxyapatite having a Ca/P ratio of 1.67 was synthesized in accordance with the well-known production process. The hydroxyapatite was sintered at 700° C. to produce granules of hydroxyapatite having a porosity of 60% and granule size of 1 to 4 mm. The thus obtained granules had an average pore size of 2 μm and specific surface area of 40 $m^2/g$.

EXAMPLE 2

A hydroxyapatite having a Ca/P ratio of 1.67 was synthesized in accordance with the well-known production process, and then spray-dried. 1000 g of the resulting hydroxyapatite power was mixed with 2000 g of 5% hydrogen peroxide water, and the mixture was foamed, dried in a drier at 100° C. and molded into a block. The block was sintered at 1200° C. A porous block having a porosity of 50% was thus obtained. The block had an average pore size of 100 to 2000 μm and specific surface area of 2 $m^2/g$.

EXAMPLE 3

A calcium phosphate having a Ca/P ratio of 1.5 was sintered at 1100° C. to produce granules of calcium phosphate having a porosity of 30% and granule size of 1 to 4 mm. The thus obtained granules had an average size of fine pores of 300 mm, average size of small pores of 8 μm and specific surface area of 12 $m^2/g$.

EXAMPLE 4

A mixture of softwood pulp and hardwood pulp in a weight ratio of 7:3 was beaten to make a pulp satisfying a Canadian Standard freeness of 360 cc. The pulp was dispersed in water to prepare a pulp slurry having a concentration of 0.3% by weight. A calcium phosphate (hydroxyapatite) having a Ca/P ratio of 1.67, specific surface area of 45 $m^2/g$ and average particle size of 2 μm was prepared in accordance with a wet process, and 0.7% by weight of the calcium phosphate was added to the pulp slurry. A paper was made in accordance with the procedure of JIS P8209. The thus obtained functional paper had a weight basis of 85 g/$m^2$ and showed a calcium phosphate content of 70% by weight.

Test Example 1

This example is intended to evaluate the deodorizing effect of the porous granules of hydroxyapatite produced in Example 1, porous blocks of hydroxyapatite produced in Example 2 and porous granules of calcium phosphate produced in Example 3.

The porous granules of Examples 1 and 3 were filled in a cylindrical container of wire mesh to make a cylindrical filter having a diameter of 60 mm and length of 100 mm. Similarly, the porous blocks of Example 2 were cylinders having a diameter of 60 mm and length of 100 mm. These cylindrical filters were used to filter an exhaust gas discharged from the automobile (displacement: 2000 cc) at a warming up mode. Before and after the filteration, a panel test for the presence of the exhaust gas smell was carried out with six pourelists. The standard for evaluating the exhaust gas smell (after filtration) is as follows.

A: smell was completely or substantially removed.
B: smell was reduced.
C: smell was not changed.
D: smell was increased.

The results of the panel test are summarized in the following Table 1.

TABLE 1

| results | panelists | | |
| --- | --- | --- | --- |
| | Example 1 | Example 2 | Example 3 |
| A | 4 | 2 | 3 |
| B | 2 | 3 | 2 |
| C | 0 | 1 | 1 |
| D | 0 | 0 | 0 |

Test Example 2

This example is intended to evaluate the deodorizing effect of the deodorant paper produced in Example 4.

The deodorant paper of Example 4 was cut to rectangular sheets having a size of 25 cm×25 cm. The deodorant sheets were disposed in a rectangular box to produce a filter device, as shown in FIG. 1. The filter device was fixed to an air outlet of an air conditioner producing malodorous air. In the presence and absence of filter device, a panel test for the presence of bad smell was carried out with six panelists. The standard for evaluating the bad smell is the same as that of the above-described Test Example 1. The results of the panel test are summarized in the following Table 2.

TABLE 2

| | evaluation | | | |
| --- | --- | --- | --- | --- |
| | A | B | C | D |
| panelists | 3 | 3 | 0 | 0 |

Note, in FIG. 1 showing the filter device, arrows indicate a direction of air flow.

EXAMPLE 5

1000 g of porous hydroxyapatite granules having an average granule size of 1.0 μm, porosity of 45%, Ca/P ratio of 1.67 and average pore size of 0.09 μm was dispersed in 1000 ml of water containing 20 g of polyvinyl alcohol to produce a slurry of hydroxyapatite. A sheet-like polyurethane foam having a thickness of 10 mm, and containing open cells with an average pore size of 300 μm and porosity of 97% was immersed in the hydroxyapatite slurry. The polyurethane foam was removed from the slurry and then dried at 25° C. A desired filter sheet was thus obtained.

EXAMPLE 6

Softwood pulp was beaten to make a pulp satisfying a Canadian Standard freeness of 650 cc.

The pulp was dispersed in water to prepare a pulp slurry having a concentration of 0.5%. A 0.5% by weight sample of porous tricalcium phosphate granules having an average granule size of 6.2 μm, porosity of 63%, Ca/P ratio of 1.5 and average pore size of 0.1 μm was added to the pulp slurry.

A paper was made in an experimental paper making machine in accordance with a handmade process. The thus obtained filter paper showed a tricalcium phosphate content of 50% by weight and a weight basis of 99 g/m².

EXAMPLE 7

900 g of porous hydroxyapatite granules having an average granule size of 1.0 μm, porosity of 45%, Ca/P ratio of 1.67 and average pore size of 0.09 μm and 100 g of porous hydroxyapatite granules having an average granule size of 10.3 μm, porosity of 60%, Ca/P ratio of 1.67 and average pore size of 1.0 μm were dispersed in 1000 ml of 3% by weight of aqueous solution of polyvinyl alcohol to prepare a slurry of hydroxyapatite. A needle-punched polyester nonwoven fabric ("Panelon" commercially available from Dynic Co.; weight: 200 g/m²) was immersed in the hydroxyapatite slurry. The nonwoven fabric was removed from the slurry and then dried at 25° C. A desired filter sheet was thus obtained.

EXAMPLE 8

400 g of porous hydroxyapatite granules having an average granule size of 2.2 μm, porosity of 50%, Ca/P ratio of 1.67 and average pore size of 0.09 μm was mixed with 600 ml a 10% by weight aqueous solution of polyvinyl alcohol. After mixing, the mixture was printed and adhered to a polyester nonwoven fabric ("Panelon" commercially available from Dynic), and then dried at 25° C. A desired filter sheet was thus obtained. Note, a printing plate used in the printing process is that containing 4 mm×4 mm squares at a distance of Test Example 3

This example is intended to evaluate the remarkably excellent deodorizing effect of the filter papers or sheets of the present invention. The deodorizing apparatus of FIG. 2 was used in conducting this evaluation.

The filter papers or sheets of Examples 5 to 8 were cut to discs having a diameter of 45 mm, and each disc, i.e., filter sheet 12a of FIG. 2, was set in a filter holder 12 of the deodorizing apparatus.

A test gas containing 14.7 ppm of ammonia ($NH_4$) in a teddler bag 11 was guided through the filter sheet 12a to a teddler bag 15. 10 liters of the test gas was passed through the filter sheet 12a. To evaluate a deodorizing effect, i.e., removal of ammonia, of the filter sheet, the concentration of the ammonia gas remaining in the filtered test gas in the teddler bag 15 was determined in accordance with an indicator tube method. The results are summarized, together with a removal percentage of ammonia, in the following Table 3. The removal percentage of ammonia means a percentage of the ammonia gas adsorbed on the filter sheet.

TABLE 3

| test gas | conc. of $NH_4$ (ppm) | removal of $NH_4$ (%) |
| --- | --- | --- |
| control (not filtered) | 14.7 | — |
| filtered with filter sheet of Ex. 5 | 5.3 | 63.9 |
| filtered with filter paper of Ex. 6 | 1.2 | 91.8 |
| filtered with filter sheet of Ex. 7 | 3.8 | 74.1 |
| filtered with filter sheet of Ex. 8 | 4.0 | 72.8 |

The results of this table indicate that 90% or more of the ammonia gas can be adsorbed on the filter sheets depending upon a specific structure thereof, and in summary, a remarkably excellent deodorizing effect can be obtained by using the filter sheets of the present invention.

Test Example 4

This example is intended to illustrate the usefulness of the filter sheets of Examples 6 and 7 as a virus adsorbent. A floating solution of influenza virus PR8 in a physiological saline was used as a test solution.

The functional paper was cut to obtain a test piece with a diameter of 5 cm. The test piece was applied onto a filter funnel, and 3 ml of the floating solution of influenza virus PR8 was poured into the funnel. The virus floating solution received from the funnel was tested to determine a titer thereof in accordance with the following method. The results are summarized in Table 4.

Determination of Titer

When the influenza virus was adhered to red blood cells, the blood cells cause their aggregation with each other. The determination of titer is made based on this aggregation reaction. Namely, the virus floating solution as a test solution is diluted with a physiological saline (0.9% aqueous solution of sodium chloride) to make a twice (2 time, 4 time, 8 time, 16 time, . . . ) increased volume, and the diluted solution is each mixed with the same amount of 0.4% floating solution of chick red blood cells. The degree of dilution at which the aggregation reaction was caused is regarded as a titer of test solution (non-diluted solution).

TABLE 4

| sample | titer |
|---|---|
| test solution (not filtered) | 128 |
| test solution filtered through the filter sheet of Example 6 | 4 |
| test solution filtered through the filter sheet of Example 7 | 32 |

Note, the titer is proportional to a concentration of influenza virus in each sample solution.

The results of the Table 4 indicate that in comparison with the virus concentration of the test solution (not filtered), virus concentration of the solution filtered through the filter sheet of Example 8 was reduced to ⅟32, and that of the solution filtered through the filter sheet of Example 7 was reduced to ¼. Namely, the influenza virus was effectively adsorbed by the filter sheets of the present invention

EXAMPLE 9

The procedure of Example 4 was repeated except that the concentration of the pulp slurry was increased to 0.5% by weight, and the concentration of the calcium phosphate added to the pulp slurry was reduced to 0.5% by weight. The obtained functional paper had a weight basis of 93 g/m$^2$ and showed a calcium phosphate content of 50% by weight.

EXAMPLE 10

The procedure of Example 4 was repeated except that the concentration of the pulp slurry was increased to 0.7% by weight, and the concentration of the calcium phosphate added to the pulp slurry was reduced to 0.3% by weight. The obtained functional paper had a weight basis of 101 g/m$^2$ and showed a calcium phosphate content of 30% by weight.

EXAMPLE 11

The procedure of Example 9 was repeated except that only the softwood pulp was beaten to make a pulp satisfying a Canadian Standard freeness of 650 cc. The obtained functional paper had a weight of basis 103 g/m$^2$ and showed a calcium phosphate content of 50% by weight.

EXAMPLE 12

The procedure of Example 11 was repeated except that a calcium phosphate (tricalcium phosphate) having a Ca/P ratio of 1.5, specific surface area of 1.5 m$^2$/g and average particle size of 1 μm was prepared in accordance with a wet process, and 0.55 by weight of the calcium phosphate was added to the pulp slurry. The obtained functional paper had a weight basis of 105 g/m$^2$ and showed a calcium phosphate content of 50% by weight.

EXAMPLE 13

The procedure of Example 11 was repeated-except that calcium phosphate (hydroxyapatite) having a Ca/P ratio of 1.67, specific surface area of 10 m$^2$/g and average particle size of 8 μm as prepared in accordance with a wet process and then sintered at 800° C., and 0.5% by weight of the calcium phosphate was added to the pulp slurry. The obtained functional paper had a weight basis of 98 g/m$^2$ and showed a calcium phosphate content of 50% by weight.

EXAMPLE 14

The procedure of Example 11 was repeated except that the pulp of Example 12 was dispersed in water to prepare a pulp slurry having a concentration of 0.3% by weight, and 0.3% by eight of the calcium phosphate was added to the pulp slurry. The obtained functional paper had a weight basis of 48 g/m$^2$ and showed a calcium phosphate content of 50% by weight.

Test Example 5

This example is intended to explain the usefulness of the functional papers of Examples 4 and 9 through 14 as a virus adsorbent.

The procedure of the above-described Test Example 4 was repeated except that the filter sheets of Examples 6 and 7 were replaced with the functional papers of Examples 4 and 9 through 14. The results are summarized in Table 5.

TABLE 5

| sample | titer |
|---|---|
| test solution (not filtered) | 128 |
| test solution filtered through paper of Example 4 | 16 |
| test solution filtered through paper of Example 9 | 32 |
| test solution filtered through paper of Example 10 | 32 |
| test solution filtered through paper of Example 11 | 16 |
| test solution filtered through paper of Example 12 | 8 |
| test solution filtered through paper of Example 13 | 32 |
| test solution filtered through paper of Example 14 | 64 |

EXAMPLE 15

This example is intended to illustrate a determination of the concentration of carbon monoxide and hydrocarbons in the exhaust gas from an automobile.

The exhaust gas discharged from an automobile (displacement: 2,000 cc) at a warming up mode was introduced into the exhaust gas filter according to the present invention. The filter used herein contained granules of hydroxyapatite having a Ca/P ratio of 1.67, granule size of 1,000 to 2,000 μm, porosity of 50% and specific surface area of 25 m$^2$/g.

Before and after the permeation of the exhaust gas filter, a concentration of carbon monoxide and hydrocarbon in the exhaust gas was determined in accordance with a conventional determination method. In this determination, a measuring instrument for simultaneously determining concentrations of the carbon monoxide and hydrocarbons (RI-503A. Qualification No. CO.HC-8, commercially available from Riken Keiki Kabushiki Kaisha)was used, and the determination time was 5 minutes. The results are summarized in the following Table 6

TABLE 6

| gas | before permeation | after filteration |
| --- | --- | --- |
| CO(%) | 5 | 1 |
| HC* (ppm) | 4,000 | 800 |

*HC: hydrocarbons

The above results indicate that the carbon monoxide and hydrocarbon gases in the exhaust gas can be remarkably reduced, if the exhaust gas is purified by using the filter of the present invention.

We claim:

1. A filter sheet which comprises a sheet-like matrix of organic polymeric material having dispersed therein a calcium phosphate compound having a molar ratio of calcium to phosphorus of 0.8 to 2.0.

2. The filter sheet according to claim 1, in which the calcium phosphate compound is selected from the group consisting of apatite, tricalcium phosphate, tetracalcium phosphate and mixtures thereof.

3. The filter sheet according to claim 1, in which the calcium phosphate compound has an average particle size of 0.1 to 2000 μm.

4. The filter sheet according to claim 1, in which the calcium phosphate compound is in the form of a porous granule.

5. The filter sheet according to claim 4, in which the porous granules have a porosity of 10 to 75%.

6. The filter sheet according to claim 1, in which the matrix of the organic polymeric material is a sheet of paper, nonwoven fabric or plastic foam.

7. The filter sheet according to claim 6, wherein said organic polymeric material comprises said sheet of paper containing 10 to 80% by weight of said calcium phosphate compound as a filler.

8. The filter sheet according to claim 7, in which the calcium phosphate compound is a secondary particle having a particle size of 0.1 to 30 μm.

9. The filter sheet according to claim 7, in which the calcium phosphate compound is selected from the group consisting of apatite, tricalcium phosphate, tetracalcium phosphate and mixtures thereof.

10. The filter sheet according to claim 7, in which the calcium phosphate compound has no coating applied onto a surface thereof.

11. The filter sheet according to claim 7, in which the calcium phosphate compound is incorporated into the paper from a slurry of pulp in water.

12. The filter sheet according to claim 7, in which the calcium phosphate compound is applied to the paper from a coating solution containing said calcium phosphate compound.

* * * * *